Figure 1:
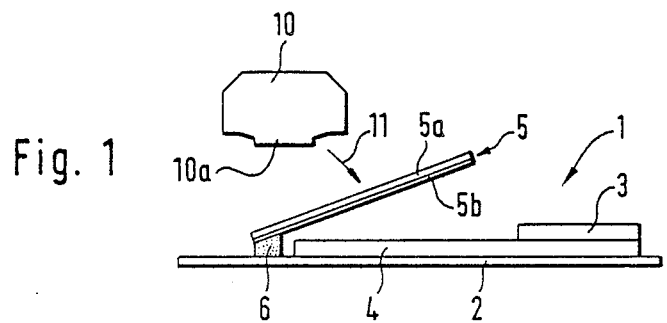

United States Patent [19] [11] Patent Number: 4,985,205
Fritsche et al. [45] Date of Patent: Jan. 15, 1991

[54] TEST CARRIER ANALYSIS SYSTEM

[75] Inventors: Rainer Fritsche, Bruhl; Klaus Nöhl, Heddesheim, both of Fed. Rep. of Germany; Klaus Pollmann, Indianapolis, Ind.; Elmar Schmidt, Bruhl, Fed. Rep. of Germany

[73] Assignee: Boehringer Mannheim GmbH, Mannheim, Fed. Rep. of Germany

[21] Appl. No.: 456,144

[22] Filed: Dec. 27, 1989

[30] Foreign Application Priority Data

Dec. 28, 1988 [DE] Fed. Rep. of Germany ....... 3844104

[51] Int. Cl.⁵ ...................... G01N 21/27; G01N 31/22
[52] U.S. Cl. ...................................... 422/56; 356/408; 422/57; 422/58; 422/67; 422/68.1; 422/116; 436/43; 436/169; 436/170
[58] Field of Search ........................ 436/169, 170, 43; 422/56, 57, 58, 68.1, 104, 63, 67, 116; 356/408

[56] References Cited

U.S. PATENT DOCUMENTS

| | | | |
|---|---|---|---|
| 4,152,390 | 1/1979 | Nosco et al. | 422/63 |
| 4,477,575 | 10/1984 | Vogel et al. | 422/57 |
| 4,523,853 | 6/1985 | Rosenbladt et al. | 250/237 R |
| 4,604,264 | 8/1986 | Rothe et al. | 422/57 |
| 4,780,280 | 10/1988 | Berger et al. | 422/56 |
| 4,780,283 | 10/1988 | Meinecke et al. | 422/58 |
| 4,839,297 | 6/1989 | Freitag et al. | 436/170 |
| 4,867,946 | 9/1989 | Gross et al. | 422/58 |
| 4,876,067 | 10/1989 | Deneke et al. | 436/169 |
| 4,910,150 | 3/1990 | Doeding et al. | 436/170 |

Primary Examiner—Robert J. Warden
Assistant Examiner—J. H. Johnston
Attorney, Agent, or Firm—Armstrong, Nikaido, Marmelstein, Kubovcik & Murray

[57] ABSTRACT

Test carrier analysis system for the analytical determination of a component of a sample fluid, in particular of a body fluid. The system comprises test carriers (1) with a color formation layer (5) which is attached movably to the test carrier. The color formation layer is in the initial state of the test carrier not in fluid contact with a fluid reservoir layer (4) likewise attached to the test carrier, but can be pressed against the latter by external manipulation. The system also incorporates an evaluation apparatus with a pressure element (10a) for the pressing of the color formation layer (5) and a control unit (25) for controlling the apparatus functions. In order to improve the analytical determination as regards simplicity of handling and accuracy of the analysis, the reference measurement and the sample measurement are under the control of the control unit (25) carried out in turn on the color formation layer serving as reference surface by means of the same optical unit (1), after the color formation layer has been pressed against the fluid reservoir layer (4) by means of the pressure element (10a).

17 Claims, 2 Drawing Sheets

TEST CARRIER ANALYSIS SYSTEM

The invention relates to a test carrier analysis system for the analytical determination of a component of a sample fluid, in particular of a body fluid, consisting of test carriers with test layers fixed to a base layer and containing a reagent system, said test layers comprising a colour formation layer and a fluid reservoir layer, where the colour formation layer is connected movably to the base layer in such a way that in the initial state of the test carrier prior to the carrying out of a determination the colour formation layer is not in fluid contact with the fluid reservoir layer, but can be pressed against the latter by external manipulation, and of an evaluation apparatus with a pressure element for the pressing of the colour formation layer against the fluid reservoir layer, an optical unit for the reflometric determination of the colour variation of the colour formation layer and a control unit for controlling the apparatus functions, where the reflometric determination includes a reference measurement in which the diffuse reflection of a reference surface is determined and a sample measurement in which the diffuse reflection of the colour formation layer is determined. The invention also relates to a corresponding method.

Whereas earlier in clinical laboratories the concentration for example of the components of the blood was determined almost exclusively by means of fluid reagents, tests using "test carriers" have gained increasing importance in recent times. In these the reagents are embedded in corresponding layers of a solid test carrier on which a drop of the sample is placed. The reaction of the sample with the reagent system leads to a colour change in the colour formation layer of the test carrier.

Evaluation apparatuses are often supplied for the test carriers, which are designed specifically for the relevant test carriers and form a test carrier analysis system with the latter. These apparatuses have an optical unit for the reflometric determination of the colour variation of the colour formation layer.

The reflometric (frequently also "reflection-photometric") measurement of the diffuse reflection (reflectivity) of a surface always necessitates a reference measurement in which the diffuse reflection of a reference surface with specified reflectivity is determined. The result of the sample measurement proper, in which the diffuse reflection of the colour formation layer is determined, is related to the reference measurement.

With test carrier analysis systems use is frequently made for the reference measurement of a special test carrier which has a test field with known reflectivity. The latter is inserted into the apparatus before each individual measurement or at least at the start of each series of measurements, in order to carry out the reference measurement. The more often this is done, the less is the risk that the measurement result will be distorted by variations in the apparatus characteristics (for example, amplifier drift, fouling of optical components, varying light scatter effects). However, since each reference measurement requires a handling step, frequent reference measurements are cumbersome. This also applies if the dry test field of a test carrier, i.e. not yet wetted by the sample, is used as reference surface, because on each occasion the test carrier has to be inserted, the reference measurement made, the sample removed and the test carrier replaced in the apparatus.

Other test carrier evaluation apparatuses operate with a reference surface that is firmly attached to the apparatus. Frequent, problem-free reference measurements are possible with the latter. The accuracy is however dependent on not only the reference surface itself, but also the "reference channel", i.e. the optical layout and electronic evaluation circuit responsible for the reference measurement, not varying in the long term. There is moreover no possibility with reference surfaces, that are firmly attached to the apparatus, of the reference properties being geared to the requirements of different test field types or test field manufacturing processes.

In order to overcome these problems, the present invention makes use of the special properties of the type of test carrier analysis systems described at the outset. The colour formation layer is mostly of the hinged type with one edge fixed to the base layer and in the initial position of the test carrier prior to the carrying out of a determination stands off obliquely from the base layer. Beneath it is disposed a fluid reservoir layer which collects the sample fluid, in most cases after it has previously flowed through some pre-stored layers.

The evaluation apparatuses of such analysis systems have a pressure element for the pressing of the colour formation layer against the fluid reservoir layer. The optical unit, the pressure element and in some cases further components of the apparatus, for example a heater for tempering the test carrier and a measurement and evaluation circuit, are controlled by means of a control unit which usually contains a microprocessor. Such test carriers are described for example in EP-A 00 45 476 (corresponding to U.S. Pat. No. 4,477,575), EP-A 0 113 896 (corresponding to U.S. Pat. No. 4,604,264), EP-A 0 267 519, EP-A 0 262 445 and EP-A 0 208 952.

Corresponding evaluation instruments are known from EP-A 75 767 (corresponding to U.S. Pat. No. 4,553,848), EP-A 00 75 766 (corresponding to U.S. Pat. No. 4,523,853) and EP-A 129 220 (corresponding to U.S. Pat. No. 4,780,283).

With such test carrier analysis systems a particularly simple and precise determination is made possible according to the invention by the fact that under the control of the control unit the reference measurement and the sample measurement are carried out in turn by means of the same optical unit on the colour formation layer also serving as reference layer, after the colour formation layer has been pressed against the fluid reservoir layer by means of the pressure element.

It has been found surprisingly that in this way a very precise quantitative evaluation of the colour formation is possible, although at the time of the reference measurement the colour formation layer is already wetted and fully permeated by the sample fluid.

Since the reference measurement and the sample measurement are carried out in turn on the same, already wetted layer, additional handling steps are superfluous. In addition a good, above-average reproducibility of the measurement results is achieved. This is due mainly to the fact that the time interval between sample measurement and reference measurement is short, the same measurement channel (i.e. the same optical unit and the same electronic circuit) is used for both measurements, and the position of the optical unit above the colour formation layer can remain unchanged. The colour formation layer serves as a comparison standard with a dual function during the reference measurement, namely for the elimination of measurement errors (like with a dual-beam process) and as a calibration standard for the reflectance measurement.

Figure 2:
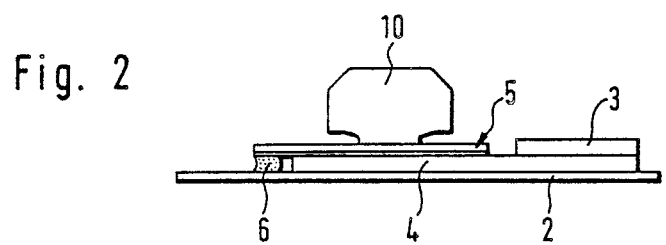
Figure 4:
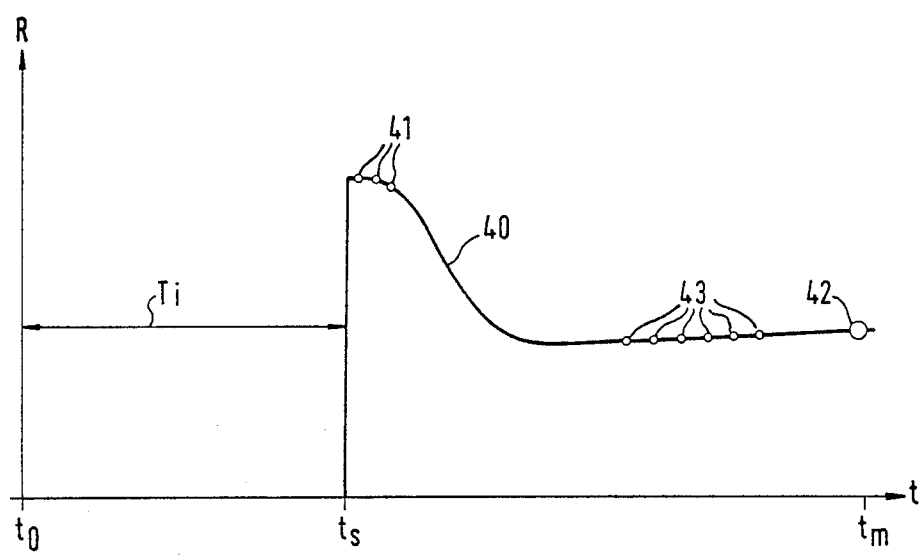
Figure 3:
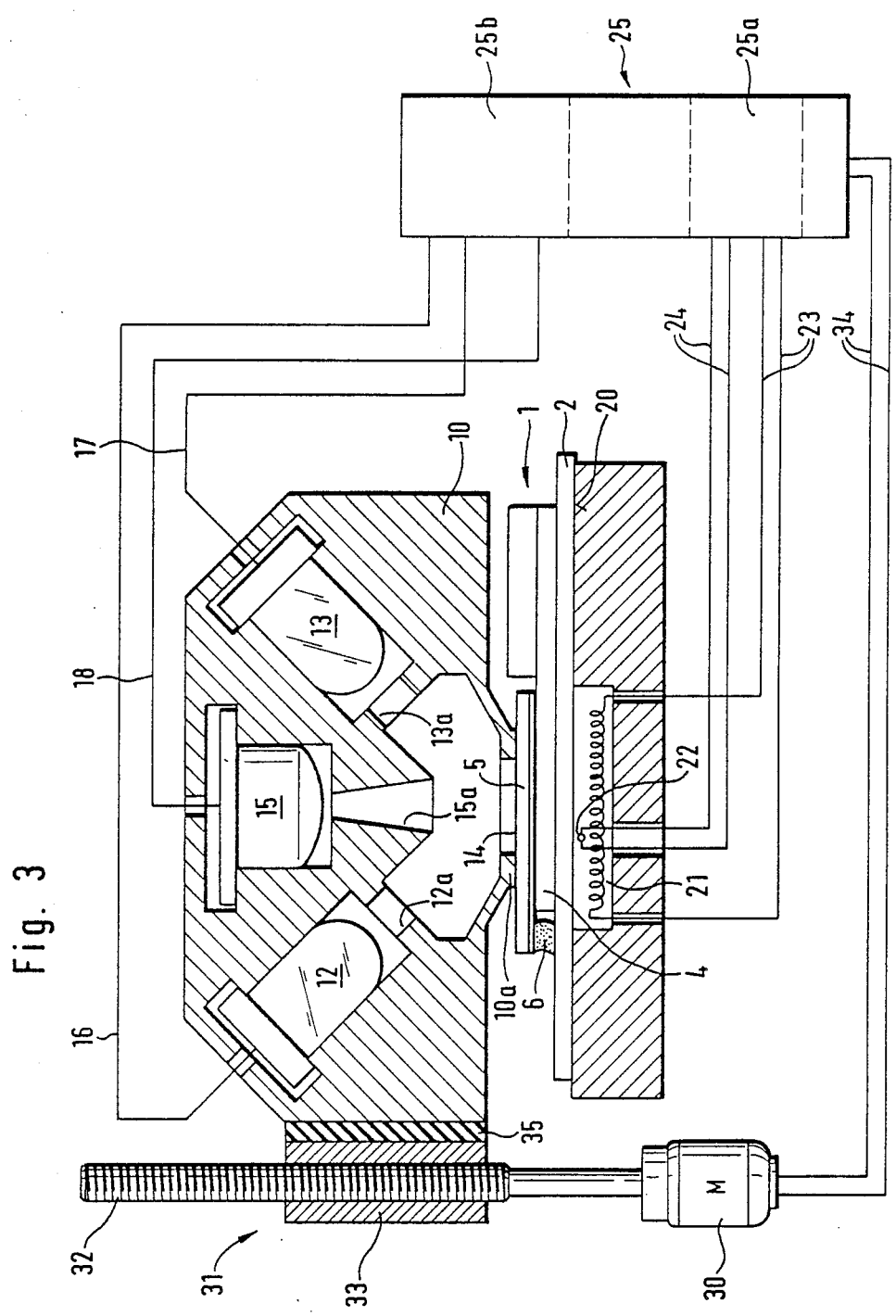

The invention will be explained in detail below by means of an exemplifying embodiment represented diagrammatically in the figures, where FIGS. 1 and 2 are side views of a test carrier and the optical unit of an associated evaluation apparatus in two different functional phases, FIG. 3 is an embodiment of the invention in a combined representation consisting of cross-section and block circuit diagram, FIG. 4 is a diagram of the time behavior of the reflectance signal for a test carrier analysis system according to the invention.

The test carrier 1 represented in FIGS. 1 and 2 comprises a longitudinal base layer 2. To the latter are fixed a pre-reaction layer 3, a fluid reservoir layer 4 and a colour formation layer 5. The colour formation layer is stuck with a hot-melt adhesive strip 6 in such a way that in the initial state prior to the carrying out of a determination represented in FIG. 1 it stands off obliquely upwards, so that it has no fluid contact with the reservoir layer 4. It consists preferably—as represented—of a transparent carrier sheet 5a, onto which a colour reaction layer 5b is coated.

The colour formation layer should have a relatively high proportion of pigment (in particular titanium dioxide) amounting to at least some 2%, preferably at least 4%. Particularly suitable for the present invention is a colour formation layer based on a plastics dispersion film, as described in EP-A 0 016 387 (corresponding to U.S. Pat. No. 4,312,834).

The colour formation layer 5 can be brought by external manipulation into a position (FIG. 2) in which fluid contact, i.e. an exchange of fluid, between the colour formation layer 5 and the liquid reservoir layer 4 is possible. This takes place with the aid of a pressure element 10a which in the represented case is part of an optical unit 10 which is movable by means of a non-represented movement mechanism in the direction of the arrow 11.

In FIG. 3 are shown further details of a test carrier analysis system, where the test carrier 1 conforms to FIG. 1.

The test carrier is positioned on a bearing surface 20 in such a way that the colour formation layer 5 is situated above a heater 21 which is monitored by means of a temperature probe 22. The heater 21 and the temperature probe 22 are connected via leads 23 and 24 to a control unit 25 which incorporates an electronic circuit 25a for the control of the heater.

The optical unit 10 shown in cross-section contains as light transmitters two light-emitting diodes 12 and 13. The diaphragm of the optical unit 10 acting as pressure element 10a surrounds in the colour formation layer 5 the measurement area 14 the diffuse reflection of which is to be measured.

The light-emitting diodes 12 and 13 are directed out of opposite directions in space diagonally onto the measurement surface 14. A light receiver, preferably a photodiode 15, is located vertically above the measurement surface. The light beams emitted by the LEDs are limited by diaphragm openings 12a, 13a. In front of the light receiver 15 diaphragm 15a is situated through which interfering marginal rays are diaphragmed out. Particular preference is given to a diaphragm according to U.S. Pat. No. 4,523,853.

The light-emitting diodes 12 and 13 and the light receiver 15 are connected via the leads 16, 17 and 18 to the control unit 25 which incorporates a measurement and evaluation circuit 25b for the triggering of the light-emitting diodes and for the amplification and processing of the signal from the light receiver 15. Such circuits are known. An example is described in European Patent Specification No. 75 767.

The optical unit 10 is movable by means of a motor 30 and a drive mechanism 31 in a direction mainly vertical to the measurement surface 14 between two positions, where in the represented lower position (corresponding to FIG. 2) the colour formation layer 5 is pressed against the fluid reservoir layer 4. In a non-represented upper position the optical unit 11 is removed from the test carrier, so that the colour formation layer 5 stands off from the latter (as shown in FIG. 1).

The drive mechanism consists in the represented case of a spindle 32 and a connecting plate 33 which is provided with a corresponding inner thread and is bolted onto the optical unit 11 via a resilient force-limiting element 35. It can however be designed in any other manner known to the expert, for example by means of suitable servomotors.

For the carrying out of an analytical determination with the test carrier analysis system according to the invention, a drop of sample fluid, in particular blood, is placed on the pre-reaction layer 3. It dissolves a reagent present there, whereby a pre-reaction takes place. Out of the layer 3 the fluid passes into the fluid reservoir layer 4, in which it spreads out. The fluid is therefore also available in the region of the layer 4 which lies beneath the colour formation layer 5. The details of the test procedure in the layers 3 and 4 depend on the respective test and are not important for the present invention. Examples can be found in the above-cited patent publications. The layer 3 can in certain cases also be omitted entirely or consist of a number of individual layers which fulfil various tasks in the test procedure. In particular an erythrocyte separation layer is suitably provided, which permits separation of the red blood corpuscles out of the blood so that plasma or serum is available for the further course of the test (cf. U.S. Pat. No. 4,477,575).

A major advantage of the represented test carrier design consists in the fact that a two-stage test procedure is possible in which the fluid first of all gets into the fluid reservoir layer 4, but there is still no contact with the colour formation layer. In this way an incubation time for a reaction occurring on the test carrier and preceding the colour formation can be established.

In FIG. 4 the time at which the test carrier is inserted into the apparatus is labelled $t_o$. Ti is the time span up to the pressing of the colour formation layer 5, i.e. the mentioned incubation time.

At the time $t_s$ (s=start) the colour formation layer 5 is pressed against the fluid reservoir layer 4 by means of the pressure element 10a, so that the fluid can escape out of the layer 4 into the layer 5 and the colour formation starts. The curve 40 shows the behavior in time of the measurement signal corresponding to the diffuse reflection R. It is seen that directly after the start time the reflectivity first of all remains almost constant, before the colour formation, which leads to a drop in the reflection signal, starts. The reference measurement is carried out at a time when the colour formation layer is fully permeated, but on the other hand the colour formation has not yet started to a significant extent.

The reference measurement consists suitably of several individual measurements (measuring points 41), from which in the simplest case a mean value is formed. Particularly in the case of tests in which the colour formation starts quickly, it may also be suitable to extrapolate backwards from the actual measurement values to the time $t_s=0$, in order to determine the diffuse reflection of the colour formation layer prior to the onset of the colour formation.

The colour formation reaction usually takes place in such a way that the reflection signal approximates asymptotically to a substantially linear course. Depending on the respective test, a specific time $t_m$ after commencement of the reaction is usually defined, at which the sample measurement is carried out, i.e. the diffuse reflection of the colour formation layer is measured and converted into the concentration of the desired analysis (so-called end point determination). This measuring point is labelled 42 in the figure.

The sample measurement, like the reference measurement, preferably consists of several individual measurement values, with savings on measuring time being possible due to the fact that these individual measurement values 43 lie prior to the time $t_m$ in a range in which a largely linear course of the colour formation curve can be expected. It is suitable for several individual measurements to be performed here and checked for linearity of the curve. If a linear course is established, extrapolation to the time $t_m$ is possible, so that the measurement can be discontinued as soon as the last of the measuring points 43 has been measured.

The procedure described is monitored by the control unit 25, so that the pressure of the colour formation layer and the optical measurements take place in a time sequence adapted to the respective test. The light-emitting diodes 12 and/or 13 and the receiver 15 are activated at the respective measuring times. The receiver signal is amplified and processed by the measurement and evaluation circuit 25b.

It is important for the invention that both during the reference measurement (measuring points 41) and during the sample measurement (measuring point 42 or measuring points 43) the diffuse reflection of the colour formation layer is determined as exactly as possible. For this reason and on account of the unavoidable inhomogeneities of the colour formation layer, it is essential to use a diffuse illumination of the measurement surface 14. The measurement surface is therefore illuminated from several directions with several light-emitting diodes which preferably have the same nominal wave-length, where the irradiation axes preferably have the same inclination to the measurement surface (preferably 30° to 60°). Known optical units for the evaluation of analytical test carriers comprise several light-emitting diodes of equal nominal wave-length which illuminate the measurement surface simultaneously, the diffuse reflection thereby obtained being determined with a measurement receiver usually located vertically above the measurement surface as in the present case.

In the context of the present invention it was however found that during the simultaneous lighting with several light transmitters several measurement errors can be caused due to the fact that the usual LEDs, even when they are of fully identical type, can have substantially different properties, particularly as regards their intensity, their wave-length and the preferred direction of the light beam in relation to the housing axis. These influences can accumulate in such a way that as a result the signal intensity produced at the receiver for one LED varies by a factor of 5 or more from another LED fitted into the same optical unit. If now the measurement surface 14 is illuminated simultaneously with both LEDs in the known manner, a correspondingly weighted averaging is obtained, i.e. the measurement signal is determined with a clear preponderance by one of the two LEDs.

In the invention it is preferable for several light transmitters contained in the optical unit to be switched on successively both during the reference measurement and during the sample measurement, so that the measurement surface is illuminated only by the light transmitter switched on at one particular time.

The respective measurement signals of the receiver thereby obtained are related to each other separately of each other for the light transmitters, in order to obtain light-transmitter-specific intermediate results from which the diffuse reflection is calculated.

If in the represented case the intensity signal usually corrected with respect to foreign light and amplifier drift (cf. e.g. EP-A-0 075 767) is labelled $I_{P1}$ for lighting with the light-emitting diode 12 for the sample measurement and $I_{R1}$ for the reference measurement and the corresponding signals for the light-emitting diode 13 are labelled $I_{P2}$ and $I_{R2}$, light-transmitter-specific intermediate results $R_1$, $R_2$ are obtained, for example by quotient formation:

$$R_1 = \frac{I_{P1}}{I_{R1}} \quad R_2 = \frac{I_{P2}}{I_{R2}}$$

The final reflectance value can then be determined algebraically, for example by simple unweighted averaging:

$$R = \frac{R_1 + R_2}{2}$$

These preferred measures enable uniform weighting of the measurement results of the individual light-emitting diodes to be achieved independently of the individual properties of the latter. This makes it possible to achieve a very good approximation to a diffuse lighting and hence a very exact determination of the diffuse reflection both during the reference measurement and during the sample measurement.

The values $R_1$, $R_2$ and R are naturally not absolute reflectance values in per cent. Reference to a reflectance standard with a reflectivity of 100% would be necessary for this. For the purposes of the evaluation of medical test carriers, however, an absolute reflectivity determination is not necessary, because the dependence of the concentration C of the sample component on R specific to the respective system is usually determined by calibration.

The references described herein above are hereby incorporated by reference for the teachings of test carriers, evaluation instruments, diaphragms, and measurement and evaluation circuits therein.

We claim:

1. Test carrier analysis system for the analytical determination of a component of a fluid sample comprising:
   test carriers comprising a base layer and test layers fixed thereto, said test layers containing a reagent system for reacting with said component to produce a detectable change and including a fluid reservoir layer and a color formation layer, the color formation layer being movably connected to the base layer to move between an initial position wherein the color formation layer is out of fluid contact with the fluid reservoir layer and a second position wherein the color formation layer is pressed against the fluid reservoir layer in fluid-exchange contact therewith, and an evaluation apparatus comprising pressure means for pressing the color formation layer against the fluid reservoir layer in fluid-exchanging contact therewith, and optical means for the reflometric determination of the color variation of the color formation layer by (a) a reference measurement wherein the diffuse reflection of the color formation layer is determined, and (b) a sample measurement in which the diffuse reflection of the color formation layer is determined, with the reference measurement and the sample measurement being conducted in turn on the color formation layer by the said optical means after the color formation layer is pressed against the fluid reservoir layer by the pressure means.

2. System of claim 1, wherein the optical means includes an optical unit means for the reference measurement and the sample measurement, and control means for controlling the optical unit means to take said measurements in turn on the color formation layer.

3. System of claim 2, wherein the reference measurement includes a plurality of successive individual measurements.

4. System of claim 2, wherein the sample measurement includes a plurality of successive individual measurements.

5. System of claim 2, wherein said optical unit means includes at least two light transmitter means which are directed onto the color formation layer from different directions in space for illuminating the color formation layer with each of the light transmitter means during both the reference measurement and the sample measurement, and the control means relates the measurement signals thereby obtained to each other for obtaining light-transmitter-specific intermediate results from which the diffuse reflection may be calculated.

6. System of claim 5, wherein said light transmitter means are light-emitting diodes.

7. System of claim 6, wherein the light-emitting diodes have substantially the same nominal wave length.

8. In a test carrier analysis system for the analytical determination of a component of a fluid sample comprising:

test carriers comprising a base layer and test layers fixed thereto; said test layers containing a reagent system for reacting with said component to produce a detectable change and including a fluid reservoir layer and a color formation layer, the color formation layer being movably connected to the base layer to move between an initial position wherein the color formation layer is not in fluid contact with the fluid reservoir layer and a second position wherein the color formation layer is pressed against the fluid reservoir layer in fluid-exchange contact therewith, and an evaluation apparatus comprising pressure means for pressing the color formation layer against the fluid reservoir layer in fluid-exchanging contact therewith, an optical means for the reflometric determination of the color variation of the color formation layer by a reference measurement, wherein the diffuse reflection of a reference surface is determined, and a sample measurement in which the diffuse reflection of the color formation layer is determined, the improvement comprising the control unit controlling the evaluation apparatus to cause the reference measurement and the sample measurement to be carried out in turn by means of the same optical unit on the color formation layer, the color formation layer also serving as the reference surface, after the color formation layer is pressed against the fluid reservoir layer by the pressure means.

9. Method for the analytical determination of a fluid sample using a test carrier having a base layer and test layers fixed thereto, with the test layers including a color formation layer and a fluid reservoir layer, and also using an evaluation apparatus which includes a pressure element by which the color formation layer may be pressed against the fluid reservoir layer, an optical unit to reflectometrically determine the color variation of the color formation layer, and a control unit for controlling the apparatus functions, said method comprising placing a fluid sample to be determined on the fluid reservoir layer while the color formation layer is out of fluid-exchange contact therewith, thereafter pressing the color formation layer into fluid-exchange contact with the fluid reservoir layer by the pressure element to cause color formation, and thereafter controlling the optical unit by the control unit to cause the same optical unit to in turn make a reference measurement and a sample measurement on the color formation layer, with the reference measurement including the determination of the diffuse reflectivity of the color formation layer directly after the layers are placed in fluid-exchange contact.

10. Method of claim 9, wherein the reference measurement includes several successive individual measurements.

11. Method of claim 9, wherein the sample measurement consists of several successive individual measurements.

12. Method of claim 9, including the steps of illuminating the color formation layer by at least two light transmitters which are directed onto the color formation layer from different spacial directions, with the color formation layer being illuminated with each of the light transmitters both during the reference measurement and during the sample measurement, and relating the measurement signals obtained thereby to each other to produce light-transmitter-specific intermediate results, and calculating the diffuse reflection from said intermediate results.

13. Method of claim 12, wherein the light transmitters are light-emitting diodes.

14. Method of claim 13, wherein the light-emitting diodes have the same nominal wavelength.

15. Method of claim 9, wherein the diffuse reflection of the color formation layer is relatively constant for a short time after the color formation layer and the fluid reservoir layers are placed in fluid-exchange contact, and thereafter the diffuse reflection value drops and then reaches a substantially constant value.

16. Method of claim 15, wherein the several successive individual reference measurements are conducted while the diffuse reflection value is relatively constant and before the said drop.

17. Method of claim 15, wherein said several successive individual sample measurements are conducted after the diffuse reflection has dropped to a substantially constant value.

* * * * *